(12) United States Patent
Boukherroub et al.

(10) Patent No.: US 8,279,444 B2
(45) Date of Patent: Oct. 2, 2012

(54) CHIPS FOR SURFACE PLASMON (SPR) DETECTION

(75) Inventors: Rabah Boukherroub, Villeneuve-d'Ascq (FR); Sabine Szunerits, Grenoble (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 798 days.

(21) Appl. No.: 11/992,808

(22) PCT Filed: Sep. 27, 2006

(86) PCT No.: PCT/EP2006/066810
§ 371 (c)(1),
(2), (4) Date: Mar. 27, 2008

(87) PCT Pub. No.: WO2007/036544
PCT Pub. Date: Apr. 5, 2007

(65) Prior Publication Data
US 2010/0149540 A1 Jun. 17, 2010

(30) Foreign Application Priority Data
Sep. 27, 2005 (FR) ...................... 05 09851

(51) Int. Cl.
*G01N 21/55* (2006.01)
(52) U.S. Cl. .................... 356/445; 438/691; 438/697
(58) Field of Classification Search .......... 356/445–448; 438/691–692, 697, 4
See application file for complete search history.

(56) References Cited

U.S. PATENT DOCUMENTS

| | | | |
|---|---|---|---|
| 3,692,816 A * | 9/1972 | Faille et al. ................... | 524/790 |
| 5,327,225 A | 7/1994 | Bender et al. | |
| 6,194,223 B1 | 2/2001 | Herrmann et al. | |
| 6,329,209 B1 | 12/2001 | Wagner et al. | |
| 7,455,816 B2 * | 11/2008 | Steuer et al. .................. | 422/102 |
| 2002/0085204 A1 | 7/2002 | Elkind et al. | |
| 2007/0059616 A1 * | 3/2007 | Mishra et al. .................. | 430/56 |
| 2007/0065998 A1 * | 3/2007 | Lee et al. ...................... | 438/166 |
| 2007/0286773 A1 * | 12/2007 | Schlautmann et al. ...... | 422/68.1 |

FOREIGN PATENT DOCUMENTS
EP  1 422 315 A1  5/2004
JP  2001-215190  8/2001

OTHER PUBLICATIONS

H. B. Liao et al.; "Preparation and Optical Characterization of Au/SiO2 Composite Films with Multilayer Structure", J. of Applied Physics, vol. 93, No. 8, Apr. 15, 2003, pp. 4485-4488.

S. Sasaki et al., "Novel Surface Plasmon Resonance Sensor Chip Functionalized with Organic Silica Compounds for Antibody Attachment", XP-001037383, Elsevier Science, 1998, pp. 71-76.

(Continued)

*Primary Examiner* — Hoa Pham
(74) *Attorney, Agent, or Firm* — Harness, Dickey & Pierce, P.L.C.

(57) ABSTRACT

The Invention relates to a method for producing a solid support coated by a metal Layer to which an $SiO_x$ layer provided with a uniform and stable thickness is applied, wherein said solid support makes it possible to determine the pretense of a compound on the surface thereof by means of Surface Plasmon Resonance ($\leq SPR \geq$).

33 Claims, 5 Drawing Sheets

OTHER PUBLICATIONS

E. Fortin et al., "Micro-Imprinting of Oligonucleotides and Oligonucleotide Gradients on Gold Surfaces: A New Approach Based on the Combination of Scanning Electrochemical Microscopy and Surface Plasmon Resonance Imaging (SECM/SPR-i)", Electroanalysis 2005, 17, No. 5-6, pp. 495-503.

R. Georgiadis et al., "Surface Plasmon Resonance Spectroscopy as a Probe of In-Plane Polymerization in Monolayer Organic Conducting Films", Am. Chem. Soc., Jul. 29, 2000, vol. 16, No. 17, pp. 6759-6762.

P. Guedon et al., "Characterization and Optimization of a Real-Time, Parallel, Label-Free, Polypyrrole-Based Dna Sensor by Surface Plasmon Resonance Imaging", Anal. Chem., vol. 72, No. 24, Dec. 15, 2000, pp. 6003-6009.

C. Jordan et al., "Surface Plasmon Resonance Imaging Measurements of Electrostatic Biopolymer Adsorption onto Chemically Modified Gold Surfaces", Anal. Chem., vol. 69, No. 7, Apr. 1, 1997, pp. 1449-1456.

D. Kambhampati et al., "Surface-Plasmon Optical Techniques", Elsevier Science Ltd., 1999, pp. 273-280.

S. Szunerits et al., "New Approach to Writing and Simultaneous Reading of Micropatterns: Combining Surface Plasmon Resonance Imaging with Scanning Electrochemical Microscopy (SECM)", Am. Chem. Soc., vol. 20, No. 21, Sep. 11, 2004, pp. 9236-9241.

A. Thiel et al., "In Situ Surface Plasmon Resonance Imaging Detection of DNA Hybridization to Oligonucleotide Arrays on Gold Surfaces", Anal. Chem., vol. 69, No. 24, Dec. 15, 1997, pp. 4948-4956.

F. Damos et al., "Determination of Thickness, Dielectric Constant of Thiol Films, and Kinetics of Adsorption Using Surface Plasmon Resonance", Am. Chem. Soc., vol. 21, No. 2, Dec. 15, 2004, pp. 602-609.

K. Peterlinz et al., "Observation of Hybridization and Dehybridization of Thiol-Tethered DNA Using Two-Color Surface Plasmon Resonance Spectroscopy", J. Am. Chem. Soc., vol. 119, No. 14, 1997, pp. 3401-3402.

H. Pyo et al., "Multichannel Surface Plasmon Resonance Imaging and Analysis of Micropatterned Self-Assembled Monolayers and Protein Affinity Interactions", Am. Chem. Soc., vol. 21, No. 1, Dec. 8, 2004, pp. 166-171.

E. Smith et al., "Surface Plasmon Resonance Imaging Studies of Protein-Carbohydrate Interactions", J. Am. Chem. Soc., vol. 125, No. 20, Apr. 26, 2003, pp. 6140-6148.

E. Smith et al., "Formation, Spectroscopic Characterization, and Application of Sulfhydryl-Terminated Alaknethiol Monolayers for the Chemical Attachment of DNA onto Gold Surfaces", Am. Chem. Soc., vol. 17, No. 8, Mar. 24, 2001, pp. 2502-2507.

L. Jung et al., "Sticking Probabilities in Adsorption of Akanethiols from Liquid Ethanol Solution onto Gold", J. Phys. Chem., vol. 104, No. 47, Nov. 2, 2000, pp. 11168-11178.

D. Kambhampati et al., "Novel Silicon Dioxide Sol-Fel Films for Potential Sensor Applications: A Surface Plasmon Resonance Study", Am. Chem. Soc., vol. 17, No. 4, Jan. 26, 2001, pp. 1169-1175.

K. Glasmastar et al., "Protein Adsorption on Supported Phospholipid Bilayers", Elsevier Science, 2002, pp. 40-47.

A. Graneli et al., "Formation of Supported Lipid Bilayer Membranes on SiO2 from Proteoliposomes Containing Transmembrane Proteins", Am. Chem Soc., vol. 19, No. 3, Jan. 9, 2003, pp. 842-850.

A. Graneli et al., "Utilizing Adsorbed Proteoliposomes Trapped in a Non-Ruptured State on SiO2 for Amplified Detection of Membrane Proteins", Elsevier, Apr. 9, 2004, pp. 498-504.

E. Reimhult et al., "Simultaneous Surface Plasmon Resonance and Quartz Crystal Microbalance with Dissipation Monitoring Measurements of Biomolecular Adsorption Events Involving Structural Transformations and Variations in Coupled Water", Anal. Chem., vol. 76, No. 24, Dec. 15, 2004, pp. 7211-7220.

B. Rothenhausler et al., "Surface-Plasmon Microscopy", Nature vol. 332, Apr. 14, 1988, pp. 615-617.

W. Knoll, "Interfaces and Thin Films as Seen by Bound Electromagnetic Waves", Annu. Rev. Phys. Chem., 1998, pp. 569-637.

M. Manesse et al., "Electrochemical Impedance Spectroscopy and Surface Plasmon Resonance Studies of DNA Hybridization on Gold/SiOx Interfaces", The Royal Society of Chemistry, Aug. 2008, pp. 1097-1103.

I. Zawisza et al., "PM IRRAS Investigation of Thin Silica Films Deposited on Gold, Part 1. Theory and Proof of Concept", Am. Chem. Soc., Jul. 28, 2007, pp. 9303-9309.

I. Zawisza et al., "Polarization Modulation Infrared Reflection Absorption Spectroscopy Investigations of Thin Silica Films Deposited on Gold. 2. Structural Analysis of a 1,2-Dimyristoyl-sn-Glycero-3-Phosphocholine Bilayer", Am. Chem. Soc., Mar. 8, 2008, pp. 39223929.

S. Szunerits et al., "Stability of the Gold/Silica Thin Film Interface: Electrochemical and Surface Plasmon Resonance Studies", Am. Chem. Soc., Jul. 13, 2006, pp. 10716-10722.

S. Szunerits et al., "Electrochemical Investigation of Gold/Silica Thin Film Interfaces for Electrochemical Surface Plasmon Resonance Studies", Electrochemistry Communications, Feb. 8, 2006, pp. 439-444.

S. Szunerits et al., "Preparation and Characterization of Thin Films of SiOx on Gold Substrates for Surface Plasmon Resonance Studies", Am. Chem. Soc., Jan. 20, 2006, pp. 1660-1663.

S. Szunerits et al., "Electrochemical Investigation of the Influence of thin SiOx Films deposited on Gold on Charge Transfer Characteristics", Electrochimica Acta, 2008, pp. 7908-7914.

\* cited by examiner

CHIPS FOR SURFACE PLASMON (SPR) DETECTION

The present invention relates to a method for producing a solid support coated with a metal layer on which a stable $SiO_x$ layer of uniform thickness has been deposited by Plasma Enhanced Chemical Vapor Deposition ("PECVD"). The invention further relates to supports thus obtained and to methods using Surface Plasmon Resonance ("SPR") in which such supports are used to determine the presence of a compound able to specifically bind to or adsorb on a target compound present on the surface of the said support. A further object of the present invention is to provide analytical kits comprising such supports and screening and selection methods of compounds of interest, using the said supports.

Surface Plasmon Resonance (SPR), which is a surface sensitive spectroscopy technique, has become, over the years, a well-accepted analytical tool for monitoring interfacial phenomena and for thin film characterization (1-9). The selectivity of this method arises from electric and magnetic field excitation on metallic surfaces of surface plasmons created at the metal dielectric interface.

Surface plasmons are excited on gold surfaces when p polarized light, undergoing total internal reflection through a prism, illuminates the gold/dielectric interface, coupling, at a certain angle, incident light to surface plasmon modes. Plasmon resonance is related to a strong decrease of the reflected light measured by a photodiode and to a resonance angle. This angle is very sensitive to any variation of the refractive index (n) of the adjacent medium and to any variation of the optical thickness. Gold and silver are ideal metal layer candidates for SPR chips operating in the visible range of the spectrum. Silver provides more distinct SPR spectra than gold and better calibrated excitation; however, it tends to be unstable in reactive environments. Therefore, gold thin films represent a better option for SPR applications in terms of stability and sensitivity. Indeed, SPR has been widely used for label-free detection, DNA hybridization reaction studies and real time detection of molecular and bio-molecular events. This can be achieved because detection is based on optical contrast variations induced by a molecule bound at the interface compared to the surrounding medium. The chemistry used for immobilizing biological compounds on the gold surface of the SPR chip is mainly based on thiolated compounds (10-15) or conducting polymers (1, 3, 8). Biacore builds bio-analytical systems based on SPR (9a). Such system use a functionalized dextran layer coupled to the gold surface to bind various chemical and biological species to the surface.

However, in many biosensor applications, silane coupling chemistry on silicon dioxide substrates is used for immobilizing bio-molecules such as DNA, hydrocarbons or proteins and their interaction with complementary analytes is detected using fluorescence techniques. However, combining fluorescence and SPR on a gold chip could not be achieved owing to the complete quenching of the fluorescence signal on gold substrates. To take advantage of SPR spectroscopy for monitoring surface reactions and coupling chemistry developed for $SiO_x$, one can coat the noble metal with a $SiO_x$ thin film. Previous attempts at developing SPR chips comprising gold layers coated with silicon dioxide thin films have already been reported in the literature. Thin silica films ($SiO_x$) have been deposited at reduced pressure or using a sol-gel technique (16). The authors observed that vapor deposited silica layers were unstable in aqueous buffer solutions such as PBS. The silica layer peels off from the metal surface within minutes of exposure in aqueous solutions. However, the sol-gel technique was successfully used to make stable $Au/SiO_x$ interfaces. The technique was based on 3-mercaptopropyl trimethoxisilane self assembly on the metallic surface followed by hydrolysis of the trimethoxisilyl groups to form surface silanol groups required for the condensation reaction of tetramethoxisilane deposited on the spinner.

Composite $Au/SiO_x$ films have been fabricated by Liao et al. in a multi-target magnetron sputtering system where the composite has been optically characterized by transmission SPR (17). Furthermore, direct functionalisation of SPR chips with γ-aminopropyl-ethoxisilane has been reported in the literature (18). Subjecting the sensor chip to silane vapor introduced terminal amino groups and led to antibody immobilization on the gold surface. The authors observed that the SPR response depended on the silane vapor SPR chip exposure time and that longer exposure times should be preferred to achieve sufficient response level. However, no comment is made on the type of binding between the gold surface and the silane multilayer (18). Graneli and Kasemo reported that stable layers could be obtained by depositing 1 nm of titanium between the gold and the silicon dioxide layers (30 nm for a SPR chip). They investigated the formation of supported phospholipid layers using a quartz crystal microbalance and SPR (19-22). In this case, a 1 nm titanium adhesion layer was necessary and the silicon dioxide film was deposited by e-beam evaporation.

Thus, in view of the above, there is a need for a simple scalable fabrication technique for depositing stable silica films on solid supports or SPR chips that will benefit the scientific community and will enable combining silane coupling chemistry with SPR spectroscopy.

This is precisely the object of the present invention.

The inventors demonstrated that plasma enhanced chemical vapor deposition (PECVD) could be used to deposit thin silica dielectric films with controlled thickness on SPR chips, in a reproducible manner. Moreover, surprisingly, the inventors demonstrated that the silica coated SPR chip thus obtained exhibits, for a thickness of about 7 nm, similar reflectivity intensity and a slightly more intense peak compared to signals obtained from a bare gold surface. The silica layers of the present invention are highly stable both in organic and in aqueous solutions and in a piranha solution at 80° C., the latter solution being eventually required to create surface silanol groups suitable for silane coupling chemistry.

Thus, the solid support coated with a metal layer covered with a stable $SiO_x$ layer of uniform thickness produced by the method of the invention described hereinafter appears to be compatible with SPR detection, enables covalent interface grafting of target molecules of interest, or can be used as a support for confined phospholipid bilayers.

Thus, the present invention relates to a method for producing a solid support coated with a metal layer on which a stable $SiO_x$ layer of uniform thickness has been deposited, the said support exhibiting noticeable response by Surface Plasmon Resonance ("SPR") and/or enabling SPR determination of the presence of a compound able to specifically bind to a target compound present on the surface of the said support, characterized in that the said $SiO_x$ layer is deposited by Plasma Enhanced Chemical Vapor Deposition ("PECVD").

Noticeable response by Surface Plasmon Resonance ("SPR") is understood here to mean the possibility for the solid support coated with a metal layer on which a $SiO_x$ layer is deposited to be used as sensor in SPR studies.

In a preferred embodiment, the said metal layer according to the production method of the present invention is selected from among gold or silver layers, gold being the most preferred one.

In another preferred embodiment, the production method according to the present invention is characterized in that the said $SiO_x$ layer deposited by PECVD has a thickness between 5 nm and 80 nm, preferably greater than or equal to nm and smaller than or equal to 40 nm or a thickness greater than or equal to 5 nm and smaller than or equal to 20 nm, most preferably a thickness equal to 7 nm±1.5 nm.

In still another preferred embodiment, the production method according to the present invention is characterized in that the said metal layer has a thickness equal to about 50 nm.

In a specific embodiment, the production method according to the present invention is characterized in that the said metal layer is coated with gold or silver particles prior to depositing the $SiO_x$ layer by PECVD.

In still another preferred embodiment, the production method according to the present invention is characterized in that the said solid support is first coated with a titanium layer, prior to being coated with the said metal layer, preferably with a thickness of about 5 nm (5 nm±1.5 nm).

In still another preferred embodiment, the production method according to the present invention is characterized in that the gas mixture used in the PECVD process is a $SiH_4$ (preferably 3% in $N_2$)/$N_2O$ mixture, preferably with respective flow rates of 260 $cm^3$/min and 700 $cm^3$/min, preferably at a substrate temperature of 300° C.

In still another preferred embodiment, the production method according to the present invention is characterized in that the $SiO_x$ coating on the support by the PECVD process is carried out at a rate of around 414 Å/min.

In still another preferred embodiment, the production method according to the present invention is characterized in that $SiO_x$ coating by the PECVD process on the support is carried out at a total reactor pressure of 1 Torr and a power of 10 W at 13.56 MHz.

In still another preferred embodiment, the production method according to the present invention is characterized in that the PECVD deposited $SiO_x$ layer has a refractive index between 1.45 and 1.48, preferably selected among 1.45; 1.465 and 1.48.

Figure 4A:
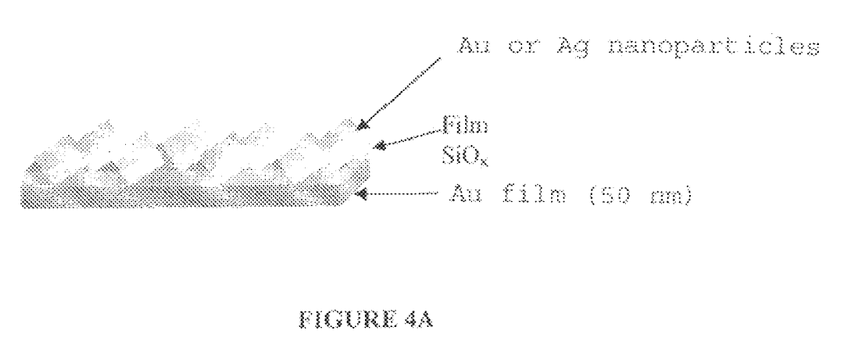
FIGS. 4A and 4B: Three-dimensional diagram representing a support on which nanoparticles of gold or silver were deposited through evaporation on an $SiO_x$ film deposited on a gold layer 50 nm thick on glass (FIG. 4A). Image obtained from scanning electron microscopy (SEM) of the surface of a support covered with an $SiO_x$ layer 10 nm thick by the PECVD technique and on which a thin layer of gold was evaporated.
Figure 4B:
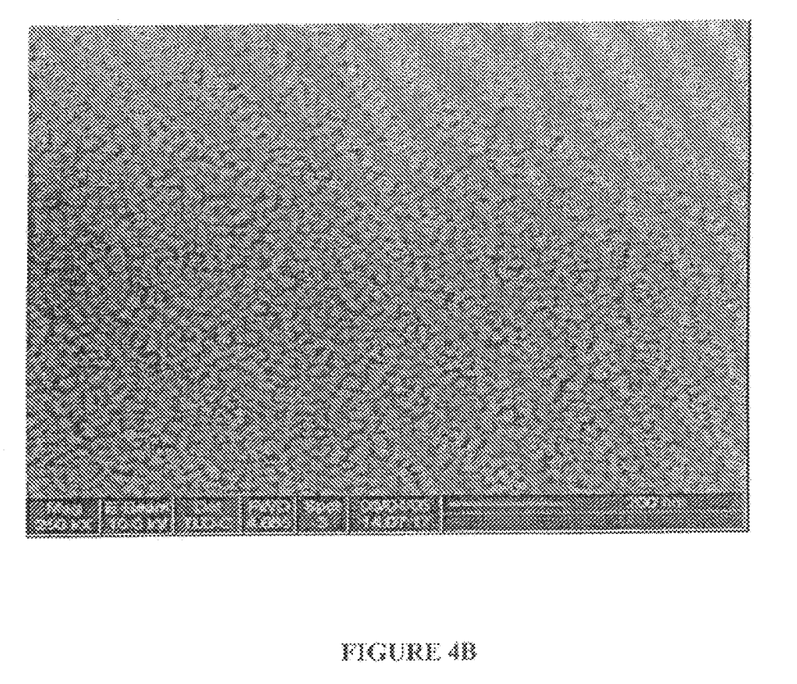

In a specific embodiment, the production method according to the present invention is characterized in that it includes an additional step of deposition, on the PECVD deposited $SiO_x$ layer, of a second metal filth, preferably of gold or silver, the said second metal layer being vaporized to form metal nanoparticles on the $SiO_x$ layer, the said second metal film preferably having a thickness smaller than 5 nm (FIGS. 4A and 4B).

Figure 5:
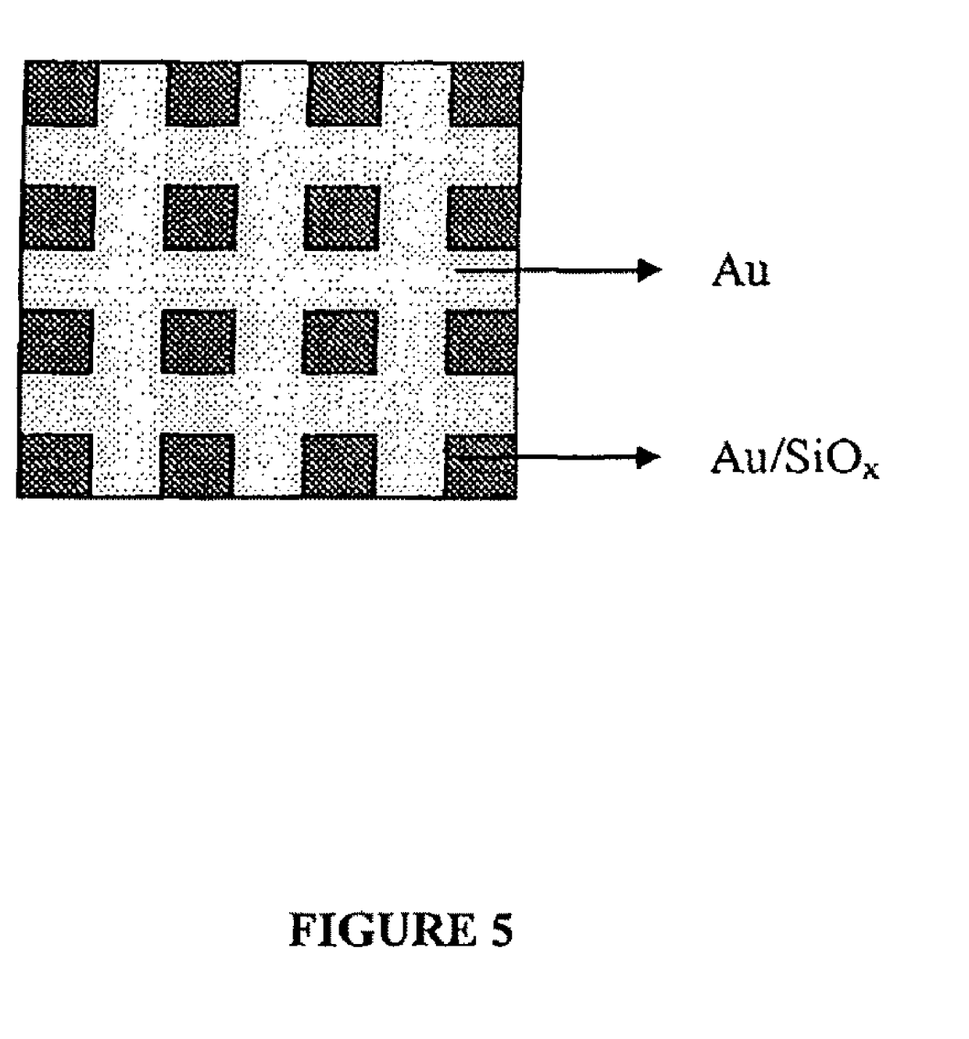
FIG. 5: Model of a support covered by an $SiO_x$ film deposited on a gold layer having a geometric configuration adapted to the imagery with SPR.

In a specific embodiment, the production method according to the present invention is characterized in that the PECVD deposited $SiO_x$ layer is deposited only on a portion of the support surface coated with the metal film, preferably according to a geometrical configuration suitable for SPR imaging. In this specific embodiment, deposition is carried out, for example, using a mask appropriate to the expected geometrical configuration. FIG. 5 shows an example of geometrical configuration appropriate to SPR imaging.

In the production method according to the present invention, the said support preferably is a transparent solid support, particularly in glass.

According to another aspect of the present invention, the invention concerns a support coated with a $SiO_x$ layer that can be obtained by the method according to the present invention, characterized in that the thickness of the $SiO_x$ layer deposited on the said support is uniform and in that the thickness of the $SiO_x$ layer and/or the SPR response is not (or are not) modified after processing the support with a piranha solution (sulfuric acid/30% hydrogen peroxide 3/1 ratio mixture) at 80° C.

The present invention also concerns a support according to the invention or obtained by a method according to the invention, characterized in that the said support has a refractive index of about 1.48 (1.48±0.4), preferably a refractive index between 1.45 and 1.48, preferably selected among 1.45; 1.465; 1.48, 1.48 being the most preferable index value.

In a preferred embodiment, the support according to the invention is characterized in that, once deposited, the $SiO_x$ layer is processed in order to produce reactive groups on the support, able to form a bond, covalent or not, with a target molecule of interest, preferably a covalent bond.

Non covalent bonds are understood here to mean ionic bonds, hydrogen bonds, Van der Waals forces or hydrophobic bonds.

Preferably, the said expected reactive groups are Si—OH groups, produced in particular by processing with a piranha solution.

The present invention also concerns a support according to the invention or obtained by a method according to the invention, characterized in that the $SiO_x$ layer is processed in a manner that enables organosilane compound coupling.

The present invention also concerns a support according to the invention or obtained by a method according to the invention, characterized in that the surface of the support on which a $SiO_x$ layer has been deposited includes functional groups of the organosilane type, preferably aminosilane, such as 3-amino-propyl trimethoxisilane and N-(2-aminoethyl))-amino-propyl trimethoxisilane or of the thiolsolane type, preferably of the mercaptosilane type, such as (3-mercapto-propyl)-trimethoxisilane.

One can, for example, refer to the WO 03/068712 international patent application published on Aug. 21, 2003, describing such glass slide functionalisation protocols with silanol Si—OH groups.

The present invention also concerns a support according to the invention or obtained by a method according to the invention, characterized in that the said target compound is attached to the said support by a covalent bond.

Preferably, the said target compound is a polypeptide, a nucleic acid or a hydrocarbon.

In the present description, polypeptide is understood to mean any compound including a peptide composed of an amino acid sequence, natural or not, of L or D shape, the said peptide compound being selected in particular among peptides, peptide-nucleic acids (PNA), lipopeptides or glycopeptides.

In the present invention, polypeptide is also understood to mean proteins or peptides, which are used indiscriminately.

Nucleic acid is understood to mean a specific nucleotide chain, modified or not, allowing the definition of a nucleic acid fragment or region including non-natural nucleotides or not, and corresponding either to double-stranded DNA, single-stranded DNA or transcription products of the said DNAs such as ARNs.

According to another aspect of the present invention, the invention concerns using a support according to the invention or obtained by a method according to the invention for determining or analyzing binding between two compounds, using SPR and/or fluorescence.

Supports or SPR chips coated with silica according to the invention exhibit a noticeable SPR response comparable to the signal obtained with a bare gold surface support. Furthermore, silica layers turn out to effectively reduce fluorescence quenching observed on bare gold surfaces. Hence, fluorescence and SPR spectroscopy can be combined using the said supports.

According to another aspect of the present invention, the invention concerns using a support according to the invention or obtained by a method according to the invention for determining or monitoring a reaction between at least two compounds, using SPR.

According to another aspect of the present invention, the invention concerns using a support according to the invention or obtained by a method according to the invention, for detecting nucleic acids, polypeptides, hydrocarbons, liposomes, vesicles or cells in a sample, preferably for detecting nucleic acids, polypeptides or hydrocarbons in a sample.

The present method is advantageously used with a support according to the invention on which the nucleic acid to be detected specifically hybridizes to a probe (target compound) present on the surface of the said support or the polypeptide or hydrocarbon to be detected specifically attaches to or adsorbs on a target compound present on the surface of the said support, the presence of nucleic acid, polypeptide or hydrocarbon being determined by SPR (See, for example, the Biacore system). The same method can be used for determining the presence of any compound of interest exhibiting specific affinity for a target compound present on the surface of the said support according to the invention.

In the case of a target compound of the polypeptide type, one could, for example, try to determine the presence of a compound of interest in a sample, capable of specifically recognizing and/or attaching to or adsorbing on this polypeptide (for example, with a antibody-antigen type bond, a ligand-receptor type bond or enzyme-substrate, etc.) Those skilled in the art will know how to use well known standard conditions and protocols for the type of specific interaction to be implemented.

According to another aspect of the present invention, the invention concerns a method for determining the presence or the amount of a compound in a sample, the said compound being able to specifically bind to or to adsorb on a target compound, characterized in that the said method includes the steps of:

a) Preparation of a support according to the invention or obtained according to a method according to the invention, on which support the said target compound is attached, preferably by covalent bonding;

b) Bringing the said support obtained at step a) in contact with the said sample expected to contain the compound capable of specifically binding to or adsorbing on the specific target compound in conditions suitable to form a specific complex between the said target compound and the said compound, the presence or the amount of which in the sample is being determined;

c) If required, at least one washing step to remove compounds not specifically attached to or adsorbed on the said target compound; and d) Determination of the presence or of the amount of the said compound in the sample using the technique called surface plasmon resonance.

According to another aspect of the present invention, the invention concerns a kit for determining the presence or the amount of a compound in a sample using surface plasmon resonance and/or fluorescence, characterized in that it includes a support according to the invention or obtained by a method according to the invention.

According to another aspect of the present invention, the invention concerns a screening method of compounds able to specifically attach to or adsorb on a given target compound, characterized in that it includes the steps of:

a) Bringing the said compound to be tested in contact with a support according to the invention or obtained by a method according to the invention, in conditions suitable for the said compound to be tested to specifically attach to or adsorb on the said support and on which support the said target compound is preferably attached by covalent bonding;

b) Removal by at least one washing step in suitable conditions, of compounds to be tested not specifically attached to or adsorb on the said target compound; and c) Selection of the tested compound if the presence of the said compound is detected by surface plasmon resonance on the support.

Finally, the present invention concerns a diagnostic or analysis instrument or device including a support according to the invention as defined above and on which a $SiO_x$ layer has been deposited by PECVD, in particular with thickness and/or homogeneity and/or stability and/or refractive index characteristics as defined above or in the following examples, or a diagnostic or analysis instrument or device including a support obtained by a method according to the present invention.

The following figure captions and examples are intended to illustrate the invention without limiting its scope in any manner.

EXAMPLE 1

Materials and Methods

1) Materials

All the cleaning and pickling reagents are of semi-conductor quality. All the chemical products are of reagent quality or higher and were used as received excluding mention to the contrary.

$C_{10}H_4F_{17}Cl_3Si$: Supplier, Gelest Inc. (11 E. Steel Rd. Morrisville, Pa.)

Isopropanol, acetone: supplier Aldrich (used without any other purification),

Hydrogen peroxide and sulfuric acid of semi-conductor quality.

2) Preparation of Gold Slides

The gold slides were prepared on the PROMESS platform from CEA of Grenoble by vacuum deposit of 5 nm of titanium and 50 nm of gold on cleaned glass slides (76×26×1 mm$^3$, n=1.58 to λ=633 nm, CML, France).

3) Preparation of Composite Gold SiO$_x$ Slides

Before the silicon film is deposited, the gold samples were all degreased in isopropanol and acetone in an ultrasonic bath at room temperature, then rinsed with abundant quantities of Milli-Q water and dried under an N-flux. The gold slides were then dried in the plasma chamber at 300° C. at a pressure of 0.005 Torr for 1 hour. SiO$_x$ layers were synthesized by deposit in vapor phase stimulated by plasma in a Plasmalab 800Plus for PECVD (Oxford Instruments). The growth conditions used were as follows: substrate temperature: 300° C., gas mixture: SiH$_4$ (3% in N$_2$) and N$_2$O (gas flow was 260 sccm and 700 sccm for SiH$_4$ and N$_2$O, respectively): total pressure in the reactor: 1 Torr; power: 10 W to 13.56 MHz. Under experimental conditions, the rate of deposit was 414 Å/min and the silicon films have a refraction index of 1.48. The thickness of the silicon films was adjusted by varying the deposit time.

4) Stability Testing

Gold samples covered by silicon layers were first rinsed with successive ultrasonication in isopropanol, acetone and deionized water at room temperature and then in 3:1 (v/v) of H$_2$SO$_4$ concentrate/30% H$_2$O$_2$ for 15 minutes, followed by abundant rinsing with Milli-Q water. The resulting samples were dried under a Z-flux.

The piranha solution reacts violently with the organic materials. It should be handled with extreme care, and followed by abundant rinsing with deionized water.

5) SPR Instrumentation

The instrument for surface plasmon resonance was an ESPRIT Autolab (Autolab, Utrecht, Netherlands) permitting simultaneous electrochemical measurements and SPR. In this work only the SPR portion will be used.

6) AFM measurements

The samples were imaged with a Dimension 3100 system AFM model (Veeco, Santa Barbara, Calif.) equipped with a nanoscope IV controller (digital instruments), at room temperature under room temperature conditions. Single-beam silicon cantilevers (AFM-TM Arrow, Nanoworld) were used with spring constants ~42 N/m and resonance frequencies of approximately ~250 kHz. All the AFM images (atomic force microscopy) were bought in operating mode at a constant force of 5 to 50 pN.

7) Ellipsometry

The spectroscopic ellipsometry data were obtained in the visible range using a UVISEL by Jobin Yvon Horiba Spectroscopic Ellipsometer equipped with DeltaPsi 2 data analysis software. The system acquired a spectrum form 2 to 4.5 eV (corresponding to 300 to 750 nm) with intervals of 0.05 eV (or 7.5 nm). Data were taken using an angle of incidence of 70° and the compensator was set to 45.0°. The data were adapted using regression analysis on a model film on a substrate as described by their thickness and complex refraction indices. The values gives in Tables 1 and 2 show an average of 5 measurements taken at different points in the surface.

8) Measurement of the Contact Angle

The contact angles of the water were measured using deionized water. A goniometry system controlled by a remote computer (DIGIDROP by GBX, France) was used to measure the contact angles. Precision is ± 2°. All the measurements were taken under ambient conditions at room temperature.

EXAMPLE 2

Results

The silicon films studied here were deposited on SPR chip surfaces using chemical decomposition of a gaseous mixture of SiH$_4$ and N$_2$O in a plasma reactor at 300° C. Under experimental conditions, the films deposited have a refraction index of 1.48 and the rate of deposit was 414 Å/min. The thickness of the film was controlled by the reaction time. Ellipsometry study of the films deposited after 10, 30, 60, 75 and 120 s resulted in thicknesses of 7.5, 20, 44, 51 and 63 nm respectively (see Table 1).

TABLE 1

Ellipsometric determination of the thickness of the SiOx layers deposited before and (A) after sonication in isopropanol/acetone/water and after 15 min of rinsing with piranha (H$_2$SO$_4$/H$_2$O$_2$: = 3/1 (v/v) (B).

| Entry | As deposited d/nm | Following treatment A[1] d/nm | Following treatment B[2] d/nm |
|---|---|---|---|
| 1 | 7.51 | 7.21 (4%) | 7.12 (1.25%) |
| 2 | 20.00 | 20.16 (0.8%) | 19.37 (3.9%) |
| 3 | 44.20 | 42.98 (2.76%) | 42.57 (0.95%) |
| 4 | 62.95 | 64.27 (2.05%) | 60.00 (6.64%) |

Figure 1A:
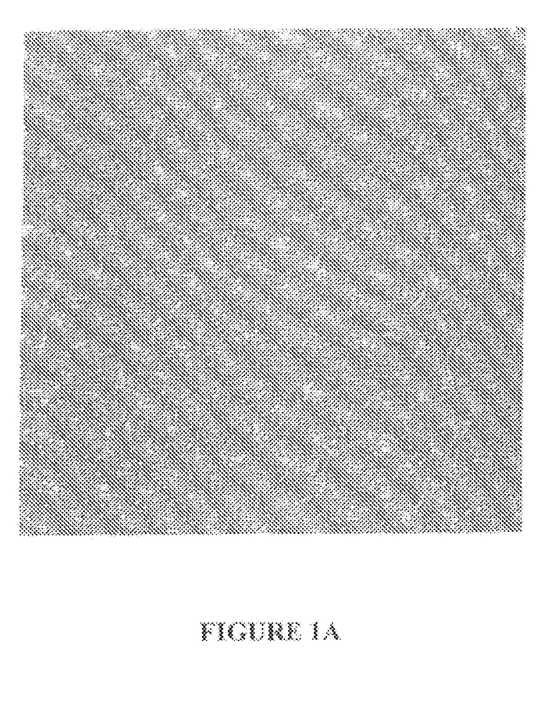
FIGS. 1A and 1B: AFM topographical images of the gold surface in tapping mode (FIG. 1A), and of surface $Au/SiO_x$ (d=7.5 nm) (FIG. 1B).
Figure 1B:
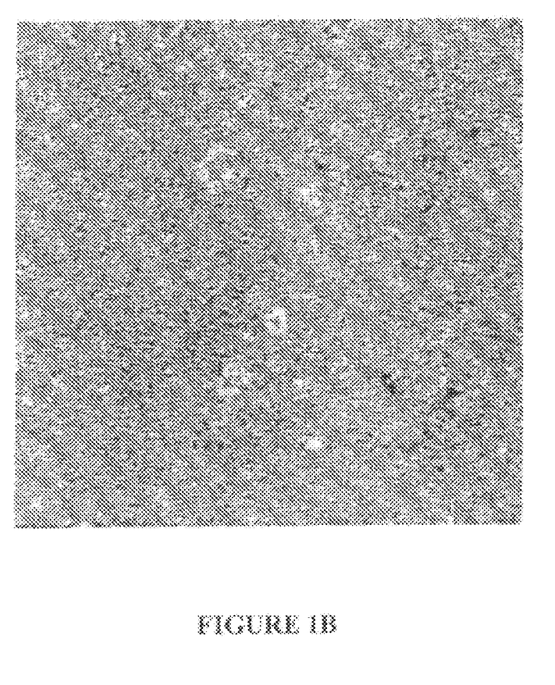

[1]successive sonication in isopropanol/acetone/water
[2]15 minutes in piranha solution The SiOx layers with thicknesses greater than 44 nm were not discussed in this study, since they do not demonstrate a significant SPR response. We then examined the topography of SPR chips before and after silicon covering. FIG. 1A demonstrates AFM in tapping mode of a cleaned gold surface. The surface is composed of grains with an average size of 40 nm and the surface roughness was found to be less than 1.8 nm. The chemical deposit of the silicon films on the surface did not cause any topographic change in the surface. The AFM image of the surface covered by a SiOx film (thickness 7.5 nm) reveals similar characteristics and the same roughness as the native surface (FIG. 1B).

Figure 2:
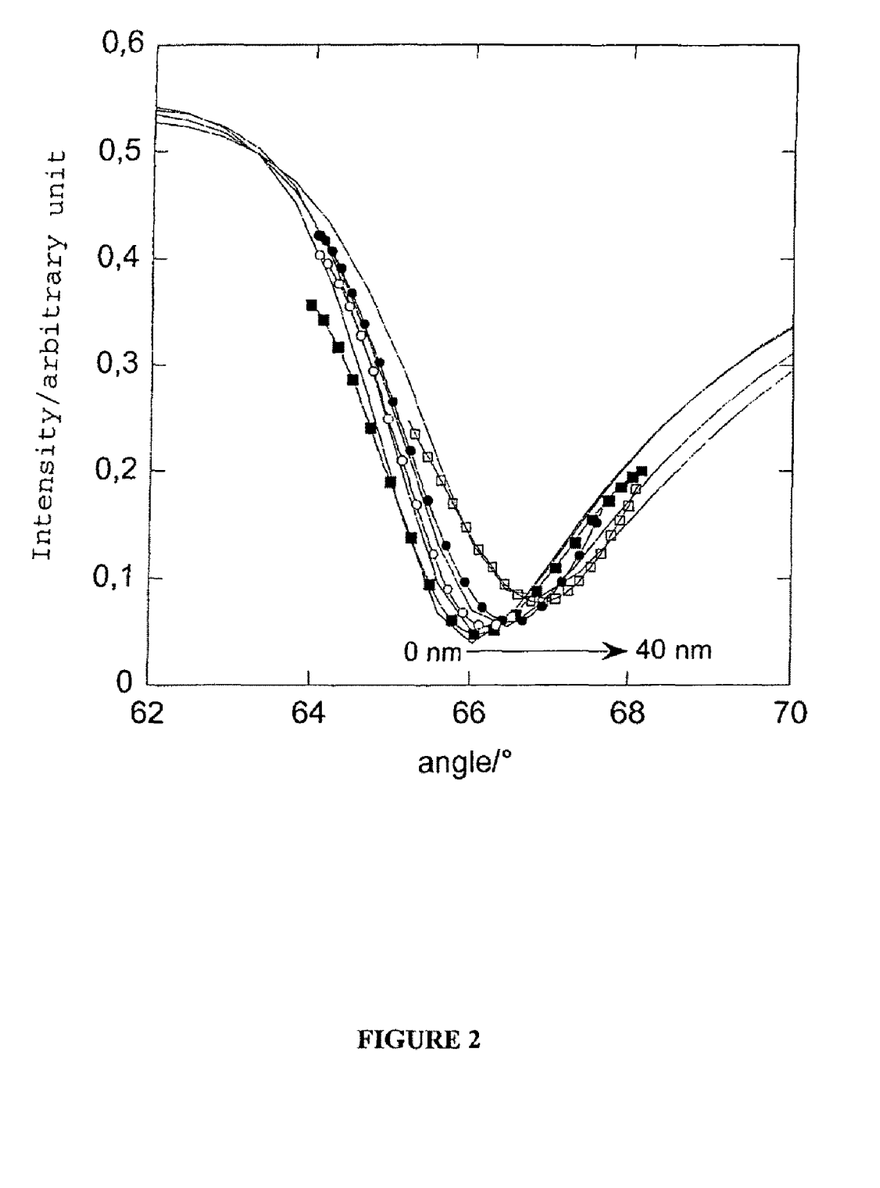
FIG. 2: Reflectivity curves against the angle of incidence for different $SiO_x$ thicknesses deposited on the gold layers 50 nm thick on glass with an adherent 5 nm titanium layer. The dotted lines are the experimental results; the solid lines are the adapted curves 0 nm (■), 7.5 nm (O), 20 nm (●), 40 (□) nm.
Figure 3:
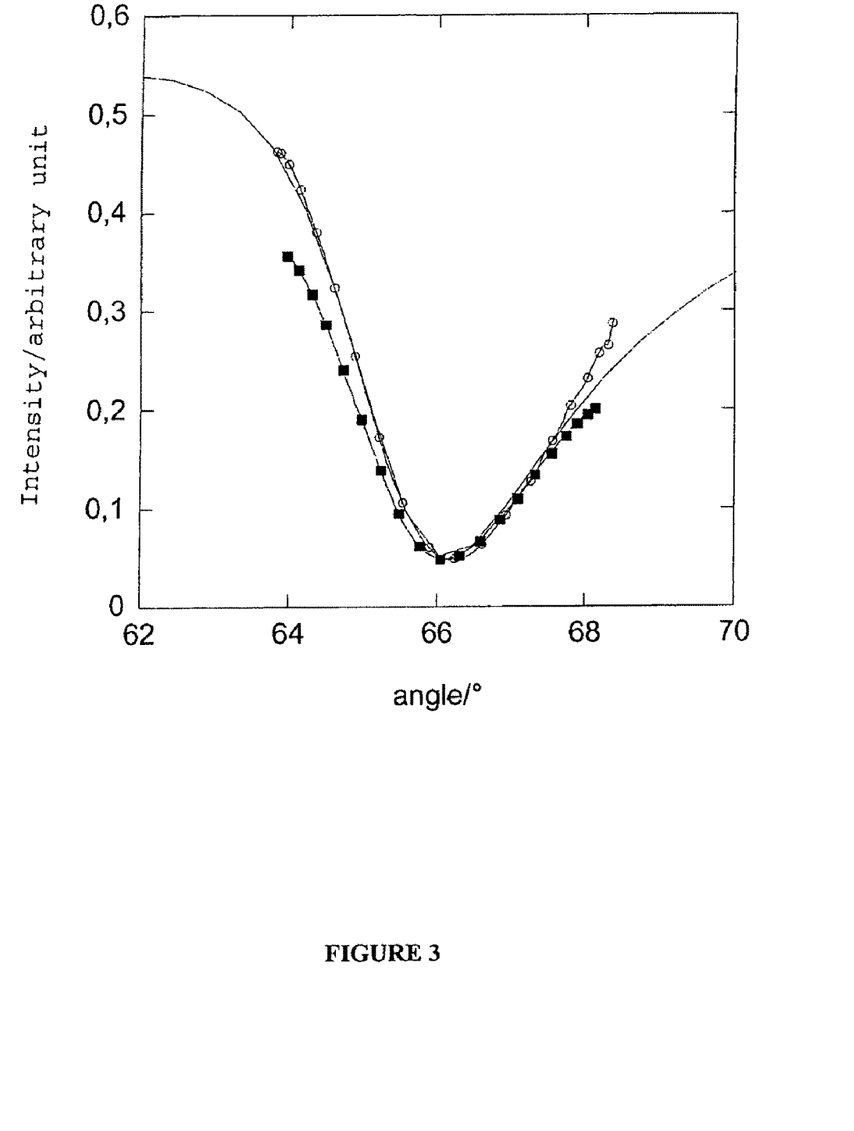
FIG. 3: Reflectivity curves against the angle of incidence for an $Au/SiO_x$ interface of 7.5 nm of $SiO_x$ on gold layers 50 nm thick on glass with a titanium adhesion layer of 5 nm. The solid line is the curve adapted for 7.5 nm of $SiO_x$ over gold; (■) is the interface after the deposit; (0) is the same surface following treatment two times with piranha at 80° C. for 15 minutes.

There are two procedures for evaluating the interfacial interactions in SPR. In the scan mode, variation of the intensity of the reflected light based on the incidence angle of the light beam is detected. The critical angle and angle of resonance are characteristic of the system to be studied and any change in the refraction index of the dielectric environment will lead to a shift in the angle of resonance toward higher angles. FIG. 2 demonstrates the shift in the angle of resonance once layers of silicon dioxide with different thicknesses (7.5 nm, 20 nm, 44 nm) have been deposited ex-situ on the glass slide covered with gold. Whereas the critical angle does not change (not demonstrated) when water is used as a solvent in all the experiments, when the minimum surface plasmon intervenes, it shifts toward higher angles with an increasing SiOx thickness: 66.03 (0 nm), 66.19° (7.5 nm), 66.45 (20 nm), 66.96 (44 nm). The silicon dioxide-gold interfaces with an SiOx thickness greater than 60 nm did not reveal a minimum SPR signal on a glass prism refraction index of 1.58 using the ESPRIT SPR Autolab instrument, since the detectable angles were outside the detectable limit. In addition to a change in the angle of resonance, the minimum resonance intensity is reduced from 0.048 (0 nm) to 0.053 (7.5 nm), 0.059 (20 nm) and 0.080 (44 nm), respectively, corresponding to an intensity dose of 0.5, 1.1, 3.2%. The experimental curves were adapted to theoretical SPR curves and the corresponding thicknesses were determined using the following parameters: n(prism) =1.58, n(gold)=0.197+i3.442 with d=530 nm, n(titanium)=2.36+i3.112 with d=60 nm, n(SiOx)=1.48.

TABLE 2

| Entry | SPR[1] As deposited | SPR Treatment[2] |
|---|---|---|
| 1 | 8 nm | 8 nm |
| 2 | 23 nm | 22 nm |
| 3 | 45 nm | 43 nm |
| 5 | — | — |

[1] the experimental curves were adapted to theoretical SPR curves by using n (prism) = 1.58, n (gold) = 0.197 + i3.442 with d = 530 nm, n (titanium) = 2.36 + i3.112 with d = 60 nm, n (SiOx) = 1.48.
[2] sonication in isopropanol/acetone/water and 15 minutes in piranha solution The results of the SPR experiments are comparable to those obtained from ellipsometric measurements in the air (7.5, 20, 4.2 nm) (Table 1). Many points were measured on the Au/SiOx interface, and the average values of d=7.51: 20.00; 44.2; 62.95 were respectively obtained.

Stability of Silicon Dioxide Films on Gold

In addition to presenting a platform compatible with SPR chips and surface functionnalization, the silicon films should support several chemical treatments to be useful for long-term studies. Therefore, the gold slides covered with silicon films were ultrasonically cleaned in isopropanol (5 minutes at room temperature), acetone (5 minutes at room temperature) and deionized water (5 minutes at room temperature). Ellipsometric analysis of the resulting surfaces did not reveal any significant evolution in the thickness of the silicon films. Only a 4% reduction in the thickness of the surface was noted (see Table 1). This analysis demonstrates the thicknesses determined by ellipsometry and SPR and confirms the film stability. This is true even when the interface is cleaned. In addition, the SPR chips covered with $SiO_x$ were demonstrated as being stable in piranha solutions ($H_2SO_4/H_2O_2$=3/1 (v/v)) for 15 minutes. Once again, less than 4% reduction in the thickness of the surface was noted (see tables 1 and 2). This may be due to the withdrawal of any absorbate or contaminant on the surface. The piranha solutions are known to decompose the organic absorbates on the surface. The ellipsometric results were confirmed by SPR spectroscopy.

Surface Functionalization

The chemical reactivity of the SPR chips covered by SiOx films was examined. The surface covered with a silicon film 7 nm wide was first of all cleaned with a piranha solution and the resulting surface was incubated in a solution of 10-2M perfluoralkylsilane for 2 hours at room temperature. The course of the reaction was followed by measurements of the angle of contact. The initial gold on glass SPR chips demonstrated a hydrophobic character with an angle of contact of 74°. Following the silicon deposit and treatment with piranha, the wetting properties of the surface changed from hydrophobic to hydrophilic. The oxidized surface had an angle of contact of the water less than 15° (similar to glass). After chemical bonding with organosilane, the angle of contact increased to 114°. This agrees with chemical immobilization of the silane molecule on the surface. This treatment proved not to induce any changes in the thickness or SPR response and produced a considerable quantity of Si—OH used to bond a trichloroperfluorosilane. To our knowledge, this is the first example demonstrating such stability in silicon films on thermically prepared gold.

The piranha treatment generated reagent surface silanol groups necessary for chemical bonding of an organosilan. This property will permit drawing advantage from surface chemistry to construct complex architectures and to introduce functional groups on the surface using the well-known surface chemistry of organosilanes.

Conclusion

Stable silicon films with thicknesses ranging from 7 to 100 nm on a metal, specifically gold may be deposited using a PECVD technique. The films are stable in corrosive environments: sonication in organic and aqueous solutions, and in piranha solutions at 80° C. The piranha treatment generated Si—OH surface groups necessary for chemical bonding to silane. The SPR chips covered by silicon films demonstrated an appreciable SPR response that can be compared to the signal obtained from a naked gold surface. The silicon layers prove to be effective in reducing inhibition of the fluorescence observed on naked gold substrates. This result will permit the combination of fluorescence spectroscopy and SPR and therefore opens up new opportunities for the detection and imaging of biomolecular events on surfaces with potential applications in diverse areas, including microfluids and biochips.

These examples demonstrate the manufacture and characterization of films with a thickness on the order of a stable nanometer of amorphous silicon (SiOx) deposited on glass slides covered with an adhesive layer of 5 nm of titanium and 50 nm of gold using a plasma-stimulated vapor-phase deposit technique (PECVD). The resulting surfaces were characterized using atomic force microscopy (AFM), ellipsometry, measurements of the angle of contact and resonance of surface plasmons (SPR). AFM analysis indicates that homogeneous silicon films with a weak roughness were formed on the gold surface. Deposited silicon films demonstrated excellent stability in different solvents and in a piranha solution. There was no significant variation in thickness or the SPR signal following these severe treatments. The silicon films with thicknesses of up to at least 40 nm permitted visualization of the effect of surface plasmons. SPR analyses also permitted determination of the thickness of silicon that were compared to ellipsometric results. A change in the contact angle for the hydrophobic gold surface and the hydrophilic Au/SiOx film. Chemical treatment with a piranha solution generated silanol surfaces that were bonded to trichlorosilane.

REFERENCES (1) Fortin, E. et al., Electroanalysis 2005, 17, 495-503.
(2) Georgiadis, R. et al., Langmuir 2000, 16, 6759-6762.
(3) Guedon, P. et al., Anal. Chem. 2000, 72, 6003-6009.
(4) Jordan, C. E. et al., Anal. Chem. 1997, 69, 1449-1456.
(5) Kambhampati, D. K. et al., Current Opinion in colloid & interface science 1999, 4, 273-280.
(6) Knoll, W., Ann. Rev. Phys. Chem. 1998, 49, 565-634.
(7) Rothenhausler, B. et al., Nature 1998, 49, 615-617.
(8) Szunerits, S. et al., Langmuir 2004, 20 9236-9241.
(9a) See: http:/www.biacore.com
(9b) Thiel, A. J et al, Anal. Chem. 1997, 69, 4948-4956.
(10) Damos, F. S. et al., Langmuir 2005, 21, 602-609.
(11) Peterlinz, K. A. et al., Am. Chem. Soc. 1997, 119, 3401-3402.
(12) Pyo, H. et al., Langmuir 2005, 21, 166-171.
(13) Smith, E. A. et al., Am. Chem. Soc. 2003, 125, 6140-6148.
(14) Smith, E. A. et al., Langmuir 2001, 17, 2502-2507.
(15) Jung, L. S. et al., J. Phys. Chem. B. 2000, 104, 11168-11178.
(16) Kambhampati, D. K. et al., Langmuir 2001, 17 1169-1175.
(17) Liao, H. B. et al., J. Appl. Phys. 2003, 93, 4485-4488.

(18) Sasaki, S. et al., Anal. Chim. Acta 1998, 368, 71-76.
(19) Glasmastar, K. et al., Colloid and Interface Sci. 2002, 246, 40-47.
(20) Graneli, A. et al., Langmuir 2003, 19, 842-850.
(21) Graneli, A. et al., Biosensors & Bioelectronics 2004, 20, 498-504.
(22) Reimhult, E. et al., Anal. Chem. 2004, 76, 7211-7220.

The invention claimed is:

1. A manufacturing process comprising:
   a) covering a solid and substantially transparent support with a metallic layer;
   b) depositing greater than 5 nm and less than or equal to 20 nm of SiOx on the support with plasma enhanced chemical vapor deposition ("PECVD"); and
   c) treating the SiOx on the support to permit covalent interface grafting on an organosilanic compound thereon.

2. Manufacturing process according to claim 1, wherein said deposited SiOx forms a layer of a uniform and stable thickness, said support permitting determination through surface plasma resonance ("SPR"), the presence of a compound capable of binding specifically to a target compound present on the surface of said support.

3. Manufacturing process according to claim 1, wherein said metallic layer is chosen from a gold or silver layer.

4. Manufacturing process according to claim 1, wherein 7 nm ±1.5 nm of said SiOx is deposited by PECVD.

5. Manufacturing process according to claim 1, wherein said metallic layer has a thickness equal to approximately 50 nm.

6. Manufacturing process according to claim 1, wherein said metallic layer is covered by gold or silver particles before the deposit of the SiOx by PECVD.

7. Manufacturing process according to claim 1, wherein said support is first covered with a titanium layer before being covered with said metallic layer.

8. Manufacturing process according to claim 1, wherein a mixture of gas used in the PECVD process is a mixture of $SiH_4$.

9. Manufacturing process according to claim 1, wherein said SiOx deposited on the support by PECVD is made at a rate of approximately 414 Å/min.

10. Manufacturing process according to claim 1, wherein the SiOx deposited on the support by PECVD is at a total pressure in the reactor of 1 T and a power of 10 W at 13.56 MHz.

11. Manufacturing process according to claim 1, wherein the $SiO_x$ deposited by PECVD has a refraction index of between 1.45 and 1.48.

12. Manufacturing process according to claim 1, further comprising an additional stage in which a second metallic film is deposited on the SiOx (deposited by PECVD) evaporated to form metallic nanoparticles on the SiOx layer.

13. Manufacturing process according to claim 12, wherein said second metallic film has a thickness of less than 5 nm.

14. Manufacturing process according to claim 1, wherein the SiOx deposited by PECVD is deposited on only one part of the support surface covered by the metallic film.

15. Manufacturing process according to claim 1, wherein said support is a solid transparent support.

16. Manufacturing process according to claim 1, wherein supports are of glass.

17. Support obtained by the manufacturing process according to claim 1, wherein the thickness of the $SiO_x$ deposited on said support is uniform and at least one of the thickness of the SiOx deposited, or the SPR response is not modified following treatment of the support with a piranha solution (mixture of sulfuric acid/hydrogen peroxide 30% in a 3/1ratio) at 80° C.

18. Support according to claim 17, wherein said support has a refraction index of approximately 1.48.

19. Support according to claim 17, wherein the SiOx layer deposited is treated after deposit in order to produce Si—OH groups.

20. Support according to claim 17, wherein the SiOx layer deposited is treated with a piranha solution.

21. Support obtained by the manufacturing process according to claim 1, wherein the support surface on which SiOx was deposited has functional groups of the organosilanic type.

22. Support according to claim 21, wherein the support surface on which SiOx was deposited has functional groups of the aminosilan type, such as the 3-amino-propyltrimethoxysilane and the N-(2-aminoethyl)-3-amino-propyltrimethoxysilane.

23. Support according to claim 21, wherein the support surface on which the SiOx was deposited has functional groups of the thiosilane type.

24. Support obtained by the manufacturing process according to claim 1, further comprising a target compound is attached by covalent bond on said support.

25. Support according to claim 24, wherein said target compound is a polypeptide, nucleic acid or carbohydrate.

26. Use of a support obtained by the manufacturing process according to claim 1, for the determination or follow-up of the reaction between at least two compounds by SPR and/or fluorescence.

27. Use of a support obtained by the manufacturing process according to claim 1, for the determination or follow-up of reactions between at least two compounds by SPR.

28. Use of a support obtained by the manufacturing process according to claim 1, for the detection in a sample of nucleic acids, polypeptides, carbohydrates, liposomes, vesicles or cells.

29. Use of a support obtained by the manufacturing process according to claim 1, for the detection of nucleic acids or polypeptides in a sample.

30. A process using a support obtained by the manufacturing process according to claim 1, with said support permitting determination through surface plasmon resonance ("SPR"), the presence of a compound capable of binding or absorbing specifically to a target compound present on the surface of said support, said process comprising:
   a) bringing said support into contact with a sample capable of containing the compound capable of binding or adsorbing specifically to said target compound under conditions appropriate for the formation of a specific complex between said target compound and said compound for which the presence or its quantity in the sample is sought to be determined;
   b) if appropriate, at least one rinsing stage in order to eliminate the compounds not specifically attached or adsorbed to said target compound; and
   c) determination of the presence or quantity or said compound in the sample by the technique called Surface Plasmon Resonance.

31. Kit for the determination of the presence or quantity of a compound in a sample using Surface Plasmon Resonance and/or fluorescence, including the support obtained by the manufacturing process according to claim 1.

32. Method for screening compounds capable of attaching or adsorbing specifically on a given target compound, the method comprising that it includes the following phases:

a) placement in contact of said compound to be tested on a support obtained by the manufacturing process according to claim 1 under conditions permitting specific attachment of said compound to be tested and on which said target compound is attached;
b) elimination by at least one rinsing stage under appropriate conditions of compounds to be tested not specifically attached or adsorbed to said target compound; and
c) selection of the compound tested if the presence of this compound is detected by Surface Plasmon Resonance on the support.

33. Diagnostic or analytical instrument or device containing the support obtained by the manufacturing process according to claim 1.

\* \* \* \* \*